US005885531A

United States Patent [19]
Heffelfinger et al.

[11] Patent Number: 5,885,531
[45] Date of Patent: Mar. 23, 1999

[54] FLUORESCENCE IMAGING INSTRUMENT UTILIZING FISH

[75] Inventors: David M. Heffelfinger, San Pablo; Franklin R. Witney, Novato, both of Calif.

[73] Assignee: Bio-Rad Laboratories, Inc., Hercules, Calif.

[21] Appl. No.: 927,556

[22] Filed: Sep. 9, 1997

Related U.S. Application Data

[63] Continuation of Ser. No. 585,303, Jan. 11, 1996, which is a continuation-in-part of Ser. No. 405,468, Mar. 16, 1995, Pat. No. 5,591,981.

[51] Int. Cl.⁶ .................................................. C12Q 1/68
[52] U.S. Cl. ..................... 422/82.05; 422/50; 422/55; 422/63; 422/68.1; 422/69; 422/82.08; 435/6; 435/283.1; 435/284.1; 435/287.1; 435/287.2; 435/289.1; 435/306.1; 435/810; 935/77; 935/78
[58] Field of Search ............... 422/50, 68.1, 55, 422/63, 69, 82.05, 82.08; 435/6, 810, 283.1, 284.1, 287.1, 287.2, 289.1, 306.1; 935/77, 78

[56] References Cited

U.S. PATENT DOCUMENTS

| | | | |
|---|---|---|---|
| 4,170,987 | 10/1979 | Anselmo et al. | 128/665 |
| 4,515,165 | 5/1985 | Carroll | 128/664 |
| 4,555,490 | 11/1985 | Merril | 436/86 |
| 4,556,057 | 12/1985 | Hiruma et al. | 128/303.1 |
| 4,786,813 | 11/1988 | Svanberg et al. | 250/461.1 |
| 4,905,169 | 2/1990 | Buican et al. | 364/525 |
| 4,922,092 | 5/1990 | Rushbrooke et al. | 250/213 |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |
| 5,121,320 | 6/1992 | Aoki et al. | 364/413.01 |
| 5,138,170 | 8/1992 | Nogouchi et al. | 250/461.2 |
| 5,190,632 | 3/1993 | Fujimiya et al. | 204/299 R |
| 5,213,673 | 5/1993 | Fujimiya et al. | 204/299 R |
| 5,242,567 | 9/1993 | Fujimiya et al. | 204/299 R |
| 5,246,866 | 9/1993 | Nasu et al. | 436/94 |
| 5,290,419 | 3/1994 | Kambara et al. | 204/299 R |
| 5,306,616 | 4/1994 | Lupski et al. | 435/6 |
| 5,427,910 | 6/1995 | Kamentsky et al. | 435/6 |
| 5,539,517 | 7/1996 | Cabib et al. | 356/346 |
| 5,563,033 | 10/1996 | Lawrence et al. | 435/6 |

FOREIGN PATENT DOCUMENTS

| | | |
|---|---|---|
| 68266 | 10/1991 | Austria . |
| 2922788 | 12/1979 | Germany . |
| 2 024 412 | 1/1980 | United Kingdom . |
| WO 90/10219 | 9/1990 | WIPO . |

OTHER PUBLICATIONS

Andersson–Engels, S., et al.; "Multicolor Fluorescence Imaging System for Tissue Diagnostics," *SPIE*, vol. 1205 Bioimaging and Two–Dimensional Spectroscopy (1990), pp. 170–189.

Tkachuk, D.C., et al. ; "Clinical Applications of Fluorescence in situ Hyrbidization," *GATA* 8(2); 67–74 (1991).

Andersson, P., et al. ; "Multispectral System for Medical Fluorescence Imaging," *IEEE Journal of Quantum Electronics*, vol. QE–23, No. 10 (Oct. 1987), pp. 1798–1805.

(List continued on next page.)

*Primary Examiner*—Ardin H. Marschel
*Attorney, Agent, or Firm*—David G. Beck; Townsend and Townsend and Crew

[57] ABSTRACT

A method and apparatus of imaging fluorescence in situ hybridization (FISH) is provided. The instrument allows the user to simultaneously acquire images from several different colors. This system, used in conjunction with a combinatorial fluorescence approach, is able to create a FISH karyotype with each chromosome being painted with a different color. The optical system is continuously tunable over the detection wavelengths. In one embodiment of the system the sample is simultaneously irradiated in more than one wavelength band and the detection system uses a common path interferometer to scan through the detection wavelengths.

29 Claims, 6 Drawing Sheets

OTHER PUBLICATIONS

Marchesini, R., et al. ; "In vivo Spectrophotometric Evaluation of Neoplastic and Non–Neoplastic Skin Pigmented Lesions –I. Reflectance Measurements," Photochemistry and Photobiology, vol. 53, No. 1, (1991), pp. 77–84.

Andersson, P.S., et al. ; "Autofluorescence of Various Rodent Tissues and Human Skin Tumour Samples," Lasers in Medical Science, vol. 2:41 (1987) ©Baillière Tindall, pp. 41–49.

Carter, N. ; "Cytogenetic Analysis by Chromosome Painting," Cytometry (Communications in CLinical Cytometry) 18:2–10 (1994).

Solioz, M. ; "Video Imaging of Ethidium Bromide–Stained DNA Gels with Surface UV Illumination," BioTechniques, vol. 16, No. 6 (1994), pp. 1130–1133.

Cothren, R.M., et al. ; "Gastrointestinal Tissue Diagnosis by Laser–Induced Fluorescence Spectroscopy at Endoscopy," Gastrointestinal Endoscopy, vol. 36, No. 2, 1990, pp. 105–111.

Product Literature for "Holographic Notch and Supernotch® Filters," Kaiser Electro–Optical Systems, Inc. (1992) 7 pp.

Rust, D.M. ; "Étalon Filters," Optical Engineering, vol. 33, No. 10, (Oct. 1994), pp. 3342–3347.

Product Literature for "SD100 & SD200 Spectral Bio–Imaging Systems," SD Spectral Diagnostics, Inc. of Agoura Hills, CA and Spectral Diagnostics (SD) Ltd. of Israel, 5 pp. 1994.

Timperman, A.T., et al. ; "Wavelength–Resolved Fluorescence Detection in Capillary Electrophoresis," Anal. Chem., (1995) vol. 67, No. 1, pp. 139–144.

Product Literature for –"FMBIO 100 –Fluorescent Imaging Device," Hitachi Software of San Bruno, CA ©1993, 6 pp.

Hood, L.E., et al. "Automated DNA Sequencing and Analysis of the Human Genome," Genomics, 1 (1987), pp. 201–212.

Bechtol, K.B., et al. ; "Using Dyes and Filters ina Fluorescent Imaging System," American Biotechnology Laboratory, (Dec. 1994), pp. 8–10.

Stevenson, C.L., et al. ; "Synchronous Luminescence: A New Detection Technique for Multiple Fluorescent Probes Used for DNA Sequencing," BioTechniques, vol. 16, No. 6, (1994), pp. 1104–1110.

Ried, T., et al. ; "Simultaneous Visualization of Seven Different DNA Probes by in situ Hybridization Using Combinatorial Fluorescence and Digital Imaging Micrscopy," Proc. Nat'l. Acad. Sci. USA, vol. 89, (Feb. 1992), pp. 1388–1392.

Rafert, J.B., et al. ; "Monolithic Fourier–Transform Imaging Sepctrometer," Applied Optics, vol. 34, No. 31, (1 Nov. 1995), pp. 7228–7230.

Lichter, P., et al. ; Analysis of Genes and Chromosomes by Nonisotopic in situ Hybridization, GATA, 8(1) ; 24–35 (1991).

Bio–Rad Laboratories Proposal—Title: Molecular Cytogenetics using the Genescope: An Ultrafast, Multicolor System for Automated FISH Analysis. Announcement No. 94–05, submitted Jul. 5, 1994, proposed start date Oct. 1, 1994. Advanced Technology Program Proposal.

FLUORESCENCE IMAGING INSTRUMENT UTILIZING FISH

This is a continuation of U.S. patent application Ser. No. 08/585,303, filed Jan. 11, 1996, which is a continuation-in-part of U.S. patent application Ser. No. 08/405,468, filed Mar. 16, 1995, now U.S. Pat. No. 5,591,981, the entire disclosures of which are incorporated herein by reference for all purposes.

BACKGROUND OF THE INVENTION

The present invention relates generally to fluorescence imaging systems and, more particularly, to a method and apparatus for fluorescence imaging in which the emission detection wavelength is continuously tunable.

In the biotechnical field, fluorescent dyes are routinely used as sensitive, non-isotopic labels. These labels are used to identify and locate a variety of cell structures such as specific chromosomes within a DNA sequence. One application, fluorescence in situ hybridization (FISH), first attaches specific chromosome regions with DNA probes and then images the probes using microscopy.

In a paper by Thomas Ried et al. entitled "Simultaneous Visualization of Seven Different DNA Probes by In Situ Hybridization Using Combinatorial Fluorescence and Digital Imaging Microscopy," *Proc. Natl. Acad. Sci. USA:Genetics,* 89 (February 1992), the authors describe a combinatorial probe labeling scheme. The disclosed technique increases the number of target sequences that can be simultaneously detected using a given number of fluorochromes. Specifically, the authors disclose simultaneously analyzing up to seven probes using only three fluorochromes.

A variety of devices have been designed to read fluorescent-labeled samples. In general, a device designed to read and/or image a fluorescent-labeled sample requires at least one light source emitting at one or more excitation wavelengths and means for detecting one or more fluorescent wavelengths.

In U.S. Pat. No. 5,290,419, a multi-color fluorescence analyzer is described which irradiates a sample with two or more excitation sources operating on a time-shared basis. Band pass filters, image splitting prisms, band cutoff filters, wavelength dispersion prisms and dichroic mirrors are use to selectively detect specific emission wavelengths.

In U.S. Pat. No. 5,213,673, a multi-colored electrophoresis pattern reading apparatus is described which irradiates a sample with one or more light sources. The light sources can either be used individually or combined into a single source. Optical filters are used to separate the fluorescence resulting from the irradiation of the sample into a plurality of fluorescence wavelengths.

In U.S. Pat. No. 5,190,632, a multi-colored electrophoresis pattern reading apparatus is described in which one or more light sources are used to generate a mixture of light capable of exciting two or more fluorescent substances. Both optical filters and diffraction gratings are used to separate the fluorescence by wavelength.

In U.S. Pat. No. 5,062,942, a fluorescence detection apparatus is described in which a fluorescent light image is separated into a plurality of virtual images. Bandpass filters are used to separate the virtual images by wavelength.

In an article by Cothren et al. entitled "Gastrointestinal Tissue Diagnosis by Laser-Induced Fluorescence Spectroscopy at Endoscopy," *Gastrointestinal Endoscopy* 36 (2) (1990) 105–111, the authors describe an endoscopic system which is used to study autofluorescence from living tissue. The excitation source is monochromatic with a wavelength of 370 nanometers. Optical fibers are used to collect the fluorescence emitted by the irradiated tissue. Emission spectra are collected from 350 to 700 nanometers using an imaging spectrograph coupled to a gated optical multi-channel analyzer. A similar autofluorescence system was described by Andersson et al. in "Autofluorescence of Various Rodent Tissues and Human Skin Tumour Samples," *Lasers in Medical Science* 2 (41) (1987) 41–49.

The above fluorescence analyzers suffer from a number of performance disadvantages. For example, all of the systems have a very limited selection of excitation wavelengths; none of them give the user the ability to specify any particular excitation wavelength. Thus these systems do not allow the user to optimize the excitation of the fluorescent label. Furthermore, the prior art systems generally detect fluorescence in discrete wavelength bands as opposed to being continuously tunable over the detection wavelengths of interest. Without the ability to continuously tune the excitation and emission detection wavelengths, the user is not able to peak the fluorescent response.

The lack of continuous tunability of the detection wavelengths in the prior art fluorescence analyzers is especially problematic in those instances in which the chosen fluorescent labels undergo spectral shifts due to external environmental effects. For example, some fluorescent probes exhibit sensitivity to solvent polarity, solvent in this context including the interior regions of various biomolecular structures (e.g., cells, membranes, proteins, etc.). This phenomena is commonly observed in fluorescent probes which have large excited-state dipole moments. Another commonly observed cause of fluorescence spectral shifts is the pH sensitivity of many fluorescent labels. Generally, pH sensitivity is the result of a reconfiguration in the probe's $\pi$-electron system.

From the foregoing, it is apparent that a fluorescence analyzer is desired which is continuously tunable over the emission detection wavelengths.

SUMMARY OF THE INVENTION

The present invention provides a continuously tunable fluorescence detection apparatus. The tunability of the apparatus resides in the ability to tune the emissions detection subassembly to any wavelength within a continuum of wavelengths.

The tuning section of the emissions detection subassembly can utilize dispersive elements, filters, or interferometers. Examples of dispersive elements are prisms and gratings. Examples of filters are short pass filters, long pass filters, notch filters, variable filters, acousto-optic filters, polarization filters, interference filters based on continuously varying film thickness, and tunable liquid crystal filters. Examples of interferometers include Fabrey-Perot etalons and common path interferometers.

In one embodiment of the invention, a look-up table determines the optimum emissions detection wavelengths and the associated bandwidths of each wavelength based upon application data provided by the user. Application data includes information such as the dye/stain/fluorochrome to be used as well as the intended sample support or separation matrix. In another embodiment of the invention, the look-up table contains information about the wavelength dependence of each of the elements within the apparatus. Using this information the user can compensate for any wavelength variations in the apparatus.

Although the emission wavelengths are well known for many fluorescent dyes, stains, and fluorochromes, various factors can result in a spectral shift of these wavelengths. In the present invention the user can compensate for these spectral shifts by tuning the emissions detection subassembly, thereby peaking the system's performance.

A fluorescence detection apparatus according to a preferred embodiment of the present invention uses a mercury arc lamp emitting from approximately 200 nanometers to approximately 650 nanometers. Different or multiple sources can be used to cover a different or larger range of wavelengths. A first filter is used to limit the light incident on the sample to those wavelengths necessary to excite the selected fluorochromes. In this embodiment all of the light emitted by sample, including both the fluorescence emitted by the probes as well as scattered incident light, passes through the first filter prior to detection. During the second pass a large percentage of the scattered incident light is removed from the emission spectra, leaving primarily the fluorescence emission spectra. If necessary a second filter is used to further refine the emission spectra prior to detection. After filtering the emission spectra passes through some means of spectral discrimination. In the preferred embodiment Fourier spectroscopy is used to separate the emission spectra into its spectral components. After exiting the interferometric stage, the light is imaged on a CCD detector array. A computer is used to perform a fast Fourier transform algorithm on the detected signals, resulting in a spectral image of the sample.

A further understanding of the nature and advantages of the present invention may be realized by reference to the remaining portions of the specification and the drawings.

DESCRIPTION OF THE PREFERRED EMBODIMENT

Fluorescence in situ hybridization (FISH) has become an important technique for visualizing DNA sequences in metaphase chromosomes and interphase nuclei. The method is now in routine use in research laboratories for gene localization studies. For example, FISH is used to map genes to specific chromosome regions or to order clones along chromosomes to create or validate clone contigs. More recently, FISH has been applied in clinical situations to detect a variety of chromosome abnormalities.

Recent efforts in FISH have focused on the development of probe technology. At present, probes are available to a variety of chromosome regions, such as teleomeres, or single-copy genes. These probes have great utility in molecular cytogenetics, with one example being the use of centromere specific probes, derived from repetitive DNA at the centromere of chromosomes, in chromosome enumeration studies. Often these repeat sequences are unique to a specific chromosome and therefore may be used to determine the number of copies of a given chromosome contained in a cell. In addition, a class of probes termed chromosome paints have recently become available. This type of probe is very useful for determining chromosome structure, as they more or less uniformly hybridize to the entire length of a given chromosome. Paints are used to determine chromosome complements of a cell, structural abnormalities such as translocations, and to identify the origin of marker chromosomes.

Numerous methods are available to label DNA probes for use in FISH, including indirect methods whereby a hapten such as biotin or digoxigenin is incorporated into DNA using enzymatic reactions. Following hybridization to a metaphase chromosome spread or interphase nuclei, a fluorescent label is attached to the hybrid through the use of immunological methods. More recently, fluorescent dyes have been directly incorporated into probes and detected without the use of an intermediate step. Standard FISH dyes include fluorescein, rhodamine, Texas Red and Cascade Blue. Multiprobe FISH analysis can be accomplished by labeling different probes with different haptens or fluorescent dyes.

The number of useful dyes for FISH is relatively limited. In order to increase the number of probes that may be imaged in a given experiment, combinatorial fluorescence approaches have been developed. In a combinatorial approach fluorescent reporter groups are used either singularly or in combination. The table below illustrates how three fluorescent reporters, A, B, and C can be used for up to seven probes. The number of detectable probes can be increased to fifteen with four fluorophores and to twenty six with five dyes.

| Probe Number | Reporter Combination |
| --- | --- |
| 1 | A |
| 2 | B |
| 3 | C |
| 4 | A + B |
| 5 | B + C |
| 6 | A + C |
| 7 | A + B + C |

Figure 1:
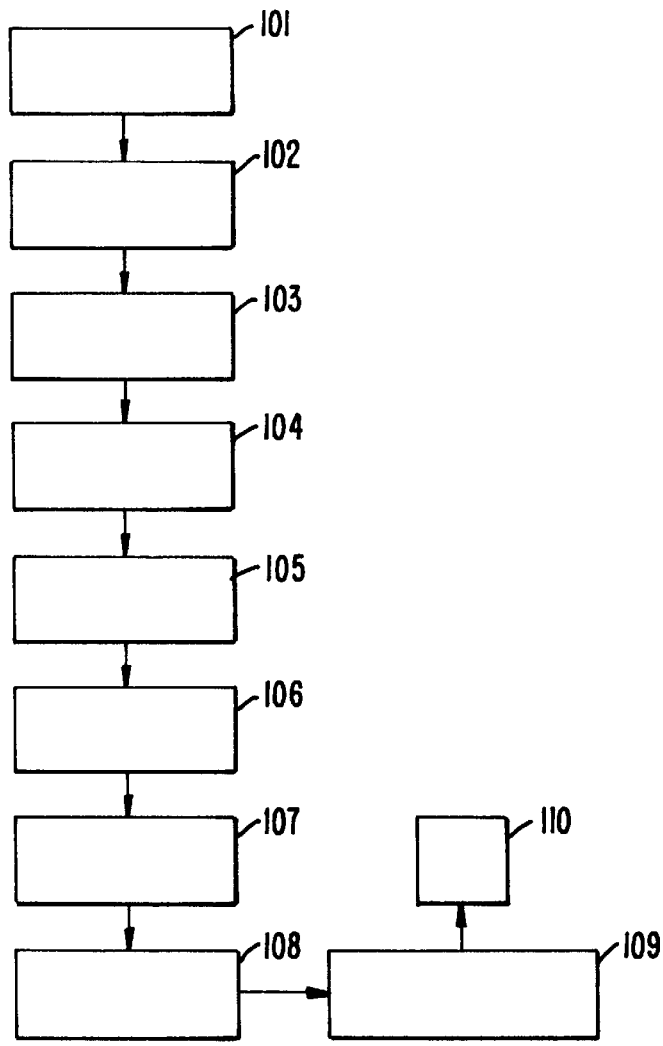
FIG. 1 is a functional block diagram of one embodiment of the invention.

FIG. 1 is a functional block diagram of one embodiment of the invention. Light from a light source 101 passes through a filter assembly 102. Filter assembly 102 removes undesired wavelengths from the light source's emission band, primarily passing the wavelengths necessary to excite the selected fluorochromes. The selected radiation then passes through condensing optics 103 prior to irradiating sample 104. The light which leaves sample 104, both emitted fluorescence as well as incident light scattered by sample 104, passes through a filter assembly 105. Filter assembly 105 removes a large percentage of the scattered light, passing selected bands of the emitted fluorescence. In some embodiments of the invention further filtering may be required. In these instances the light exiting filter 105 is passed through a second filter assembly 106. The filtered fluorescence spectra then passes through a spectral discriminator 107 prior to being imaged using a megapixel charge coupled device (CCD) array 108. Signals from the CCD array are sent to a computer 109 which is used to construct images of sample 104. The images are presented on a CRT screen 110.

Figure 2:
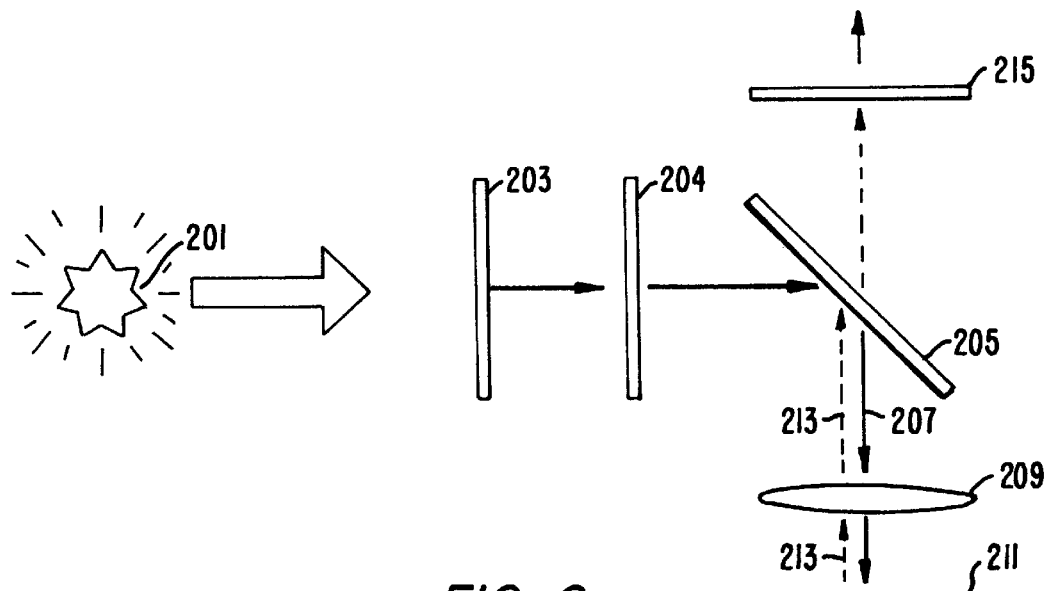
FIG. 2 is an illustration of one aspect of the optical train in one embodiment of the invention.

FIG. 2 is an illustration of one aspect of the optical train in one embodiment of the invention. Light emitted from a source 201 first passes through optional broadband filter 203. Filter 203 is used to remove large bands of undesirable radiation. For example, filter 203 can be used to remove IR radiation, assuming that the selected fluorochrome is not excited by IR radiation. The light then passes through filter 204 which transmits primarily the wavelengths necessary to excite the selected fluorochromes. The light next impinges on a beamsplitter 205 which reflects the wavelengths necessary to excite the selected fluorochromes while passing the undesirable wavelengths. The reflected radiation then passes along light path 207, through condensing optics 209, and impinges on sample 211. The incident light causes the fluorochromes on the various probes to fluoresce, the emitted fluorescence following path 213. Also following path 213 is light which was scattered by sample 211. In order to accurately measure the emitted fluorescence, the scattered radiation must be removed. The light leaving sample 211 and following path 213 is incident on beamsplitter 205. Since the reflection coating on beamsplitter 205 is designed to reflect those wavelengths necessary for exciting the selected fluorochromes while passing all other radiation, beamsplitter 205 removes the scattered light by reflecting it away from path 213 while passing the emitted fluorescence. The emitted fluorescence is further filtered using filter 215. At this point the light is ready for spectral dissection.

After the emitted fluorescence has been properly filtered, there are a number of techniques which can be used to spectrally discriminate the emitted fluorescence spectra, thereby distinguishing between the different probes. These techniques fall into two categories: dispersive elements and filters.

Figure 3:
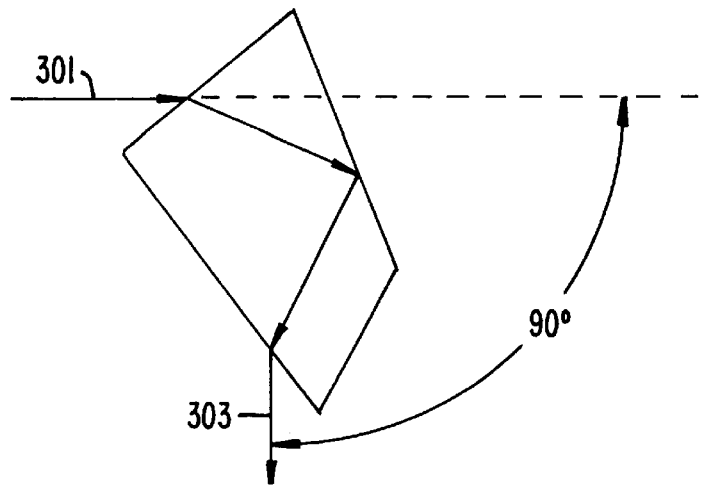
FIG. 3 is an illustration of a Pellin-Broca prism.

A prism is a dispersive element which, in its standard form, is non-linear as a function of deviation. This non-linearity results in a rather complex optical apparatus design. Therefore to minimize the complexity of the optical design, it is preferable to use a constant deviation dispersing prism such as the Pellin-Broca prism shown in FIG. 3. In this type of prism a single monochromatic ray 301 will pass through the prism and exit at a deviation of 90 degrees from the initial incident beam 303. All other wavelengths will emerge from the prism at different angles. By rotating the prism along an axis normal to the plane of the image in FIG. 3, the incoming ray will have a different angle of incidence and a different wavelength component will exit the prism at a deviation of 90 degrees. This type of prism obviously simplifies the design of the apparatus since the system can operate at a fixed angle and the wavelength can be tuned by rotating the prism.

Figure 4:
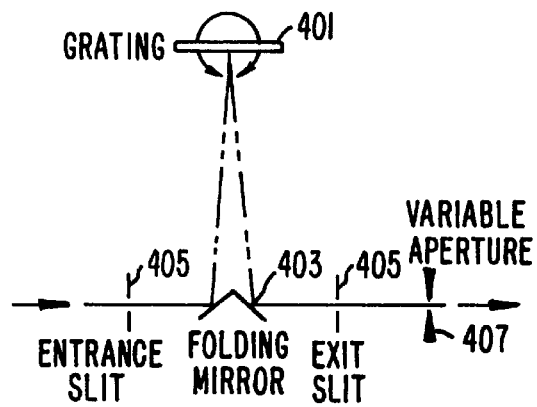
FIG. 4 is an illustration of a wavelength dispersive system using a grating.

A grating can also be used to spectrally disperse the emitted fluorescent spectra. FIG. 4 shows one configuration of a wavelength dispersive system comprising grating 401, folding mirror 403, entrance and exit slits 405, and aperture 407. The wavelength is tuned by rotating grating 401. The bandwidth of this system is a function of the grating groove spacing, the aperture diameter, and the distance between the aperture and the grating. In the preferred configuration of this embodiment multiple gratings are used which can be remotely selected depending upon the wavelength region of interest. Using multiple gratings insures that sufficient radiation is collected within all of the spectral bands of interest.

Figure 5:
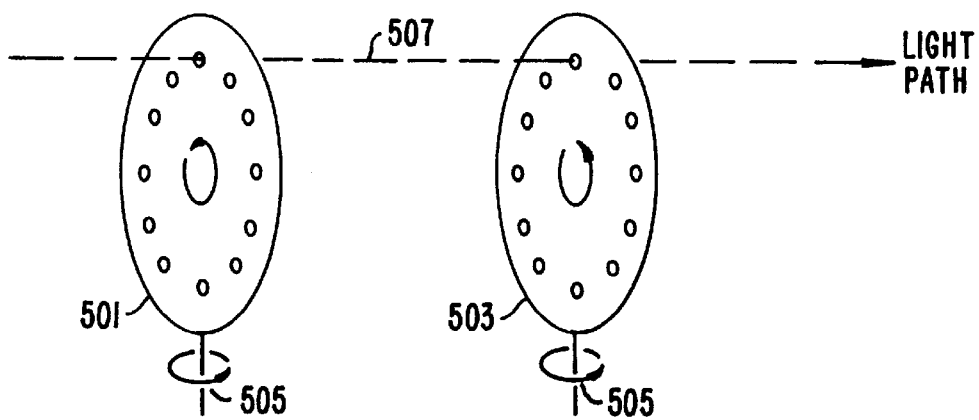
FIG. 5 is an illustration of a dual filter wheel approach to obtaining wavelength tunability.

Another approach to tuning the detection wavelength is to use optical filters. In FIG. 5 a filter wheel 501 contains a series of filters with a short pass edge while a filter wheel 503 contains a series of filters with a long pass edge. Therefore both the wavelength as well as the bandwidth is determined by the choice of filters. For example, by selecting a short pass filter of 450 nanometers and a long pass filter of 470 nanometers a 20 nanometer band centered at 460 nanometers is selected. In order to insure that the wavelength is continuously tunable, filter wheels 501 and 503 not only rotate to allow the selection of a particular filter, but they also can be rotated about axes 505. This results in the filters being tilted with respect to optical axis 507. As the filters are tilted off-axis their wavelength characteristics gradually change.

Another approach to tuning the wavelength is to use variable filters. Circular variable filters are simply interference filters in which the film thickness varies linearly with the angular position on the substrate. An embodiment using circular variable filters would be similar in appearance to the configuration shown in FIG. 5 except that filter wheels 501 and 503 are replaced with the circular variable filters. Depending upon the position of each filter wheel and the tilt along axes 505, any wavelength can be chosen. By controlling the amount of light illuminating the filters, through the use of slits, the bandwidth can also be controlled.

In another embodiment of the invention, a Fabrey-Perot etalon tunable filter can be used to tune the detection wavelength. In this embodiment it is generally preferable to eliminate most of the undesired wavelengths using a band-pass filter. Then the fine tuning is performing using the Fabrey-Perot system. In a variation of this system, ferro-electric liquid crystal devices can be inserted into the interference filters of the Fabrey-Perot etalon. This design is capable of high throughput as well as rapid fine tuning of the system.

Figure 6:
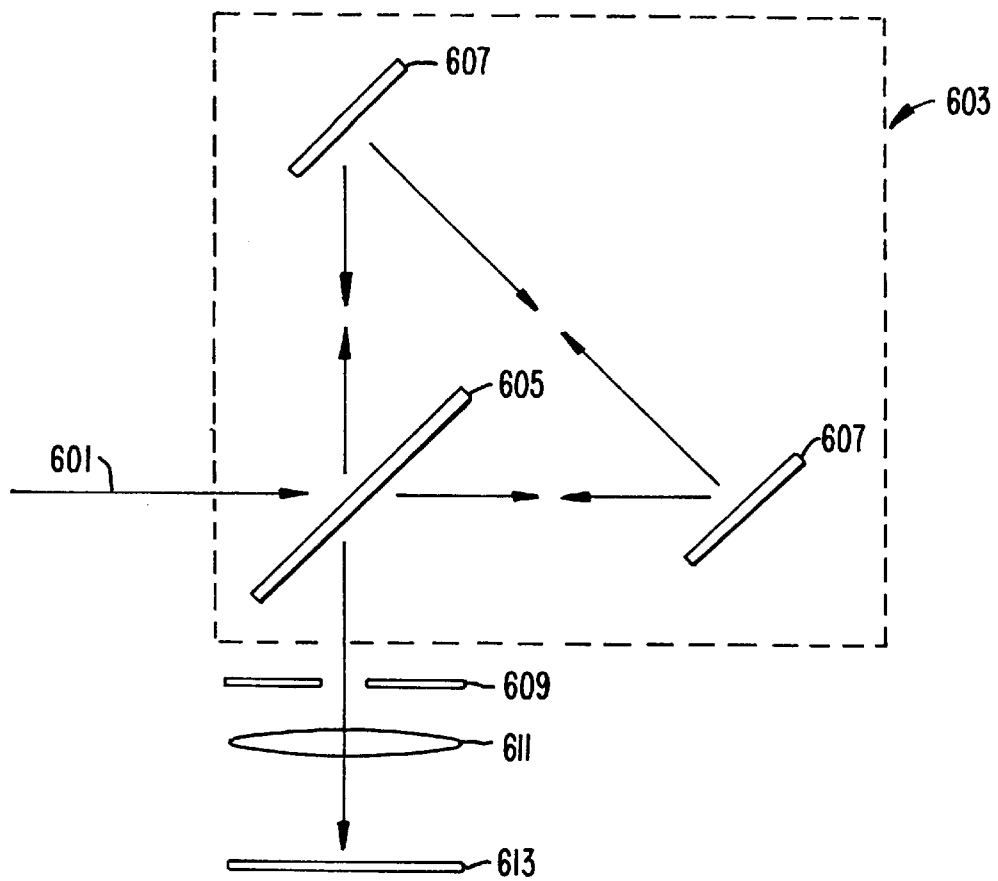
FIG. 6 is an illustration of a SAGNAC interferometer.

The preferred embodiment of the emission detection system is shown in FIG. 6. In this embodiment after the fluorescence emitted from the sample is filtered to remove much of the undesired wavelength spectra, it enters a SAGNAC interferometer 603. SAGNAC interferometer 603 is comprised of a beam splitter 605 and turning mirrors 607. Wavelength selection is accomplished by controlling the optical path difference of the interferometer. Adjustable slit 609 controls the bandwidth. Optics 611 focus the radiation passing through the interferometer and produce a real image onto detector 613. In this embodiment detector 613 is a CCD array and there is a one to one correspondence between the sample and the projected image of the sample.

As illustrated in FIG. 6, beamsplitter 605 divides the incoming light into two separate beams. These beams are recombined to form an interference pattern at detector array 613. The pattern's intensity at each pixel of array 613 varies with the optical path difference. By measuring the intensity versus the optical path difference, an interferogram is created. In order to recover the wavelength spectra at each pixel of array 613, a Fourier transform of each interferogram is calculated. The Fourier transform is calculated using computer 109.

Figure 7:
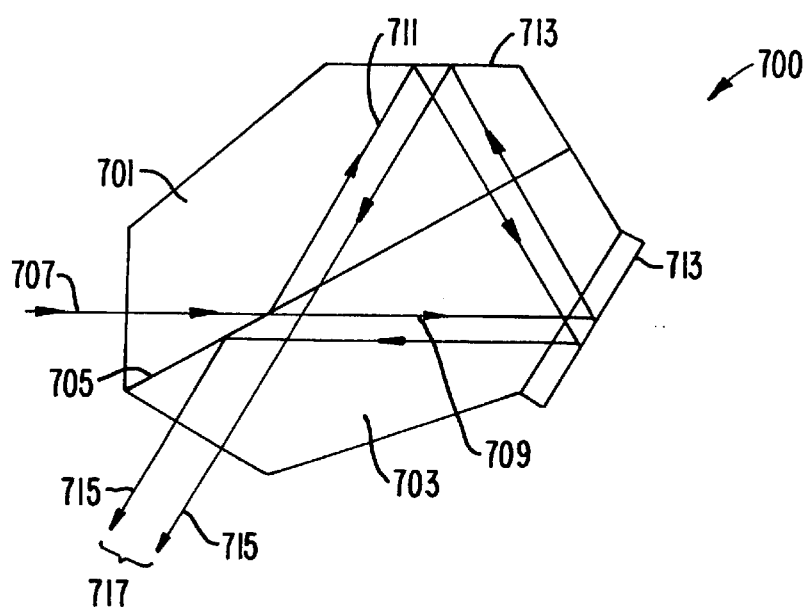
FIG. 7 is an illustration of a monolithic interferometer.

FIG. 7 illustrates a monolithic form of interferometer 700 which can also be used with the present invention in place of interferometer 603 shown in FIG. 6. The monolithic interferometer is more immune to vibration, misalignment, and thermal effects then other forms of interferometer. This form of interferometer also has a very large acceptance angle.

Interferometer 700 is comprised of a first piece of glass 701 bonded to a second piece of glass 703 along the plane of a beamsplitter coating 705. Light is incident on the interferometer along path 707. When this light ray hits beamsplitter coating 705, the ray is split into two rays, one ray following path 709 and the other ray following path 711. After being reflected by interferometer mirrors 713, the rays exit the optic along paths 715 separated by a distance 717.

Once the spectral data for each pixel of array 613 has been determined, computer 109 can be used to generate a variety of useful images on screen 110. The identified probes can be viewed either individually or in a variety of combinations, including showing all identified probes simultaneously. Thus, if at least five different dyes are used, it is possible to create a FISH karyotype with each chromosome individually identified. Since many of the probes will contain multiple dyes (i.e., combinations of dyes in a single probe), pseudo-coloring can be used to simplify the presented image. In this scheme each probe is assigned an easily distinguishable color. For example, if three dyes were used to form seven probes, four of the probes would be formed by some combination of dyes. By assigning each probe, including those with multiple dyes, an individual color, the image presented to the user is quite simple and straightforward. The computer can also be used to enhance the image as well as provide intensity profiles (e.g., different colors assigned to different measured intensities).

In one embodiment of the invention computer 109 includes a look-up table. This table can be used to instruct the user as to the optimum system operating parameters (i.e., excitation and emission wavelengths, excitation and emission bandwidths, etc.) for a specific experimental configuration (e.g., particular probe or dye). The look-up table can also be used to compensate for variations in the system. For example, each element of the optical train, from the source to the detector, is likely to exhibit some degree of wavelength dependence. Therefore to distinguish the emission intensities for two different dyes solely on the observed intensity differences would be in error. Using the look-up table the variational information can be programmed into the system, thus allowing the system to automatically correct the final image for system variations.

In another embodiment of the invention, the look-up table contains a library of predetermined spectral data. By comparing the spectral data determined by computer 109 after performing the Fourier transform to the data in the look-up table, the identity of the individual labels can be determined. The look-up table can also be used to compare measured interferograms with predetermined interferograms, using the results of this comparison to identify the various chromosome labels. Using the latter approach removes the necessity of calculating the Fourier transform of the data.

Figure 8:
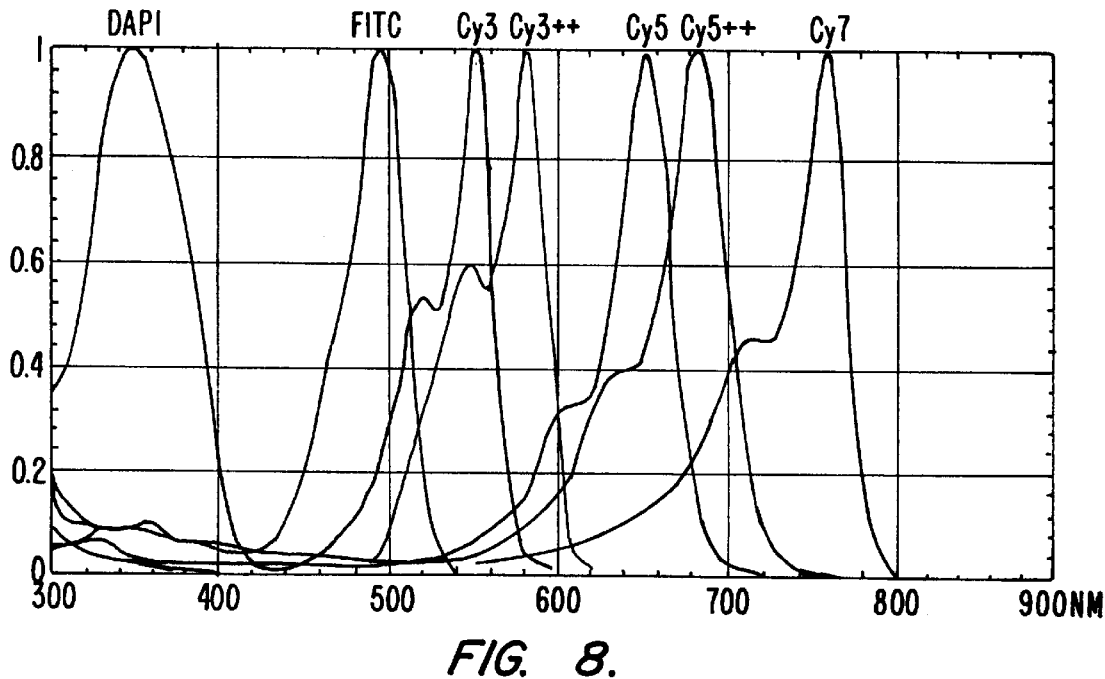
FIG. 8 is a graph of the normalized fluorescence excitation spectra for seven different fluorochromes.
Figure 9:
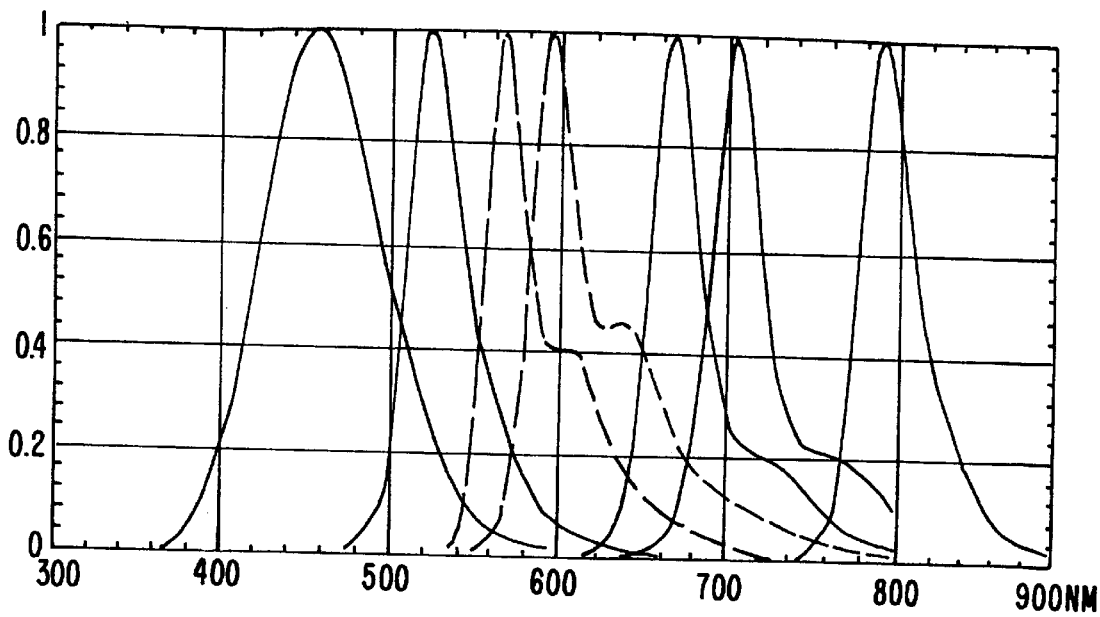
FIG. 9 is a graph of the normalized fluorescence emission spectra for the seven fluorochromes shown in FIG. 8.

FIGS. 8 and 9 are normalized fluorescence excitation and emission spectra for seven different fluorochromes, respectively. As previously described, due to the intense Rayleigh scattering of the excitation light from the sample, it is necessary to design filters which are able to sufficiently block the excitation wavelengths while exhibiting high throughput in selected regions of the emission wavelength bands. Such filters are possible because of the spectral shift between the excitation and emission wavelengths. However, as the number of fluorochromes and therefore the number of possible probes increases, the difficulty in designing such filters also increases.

Figure 10:
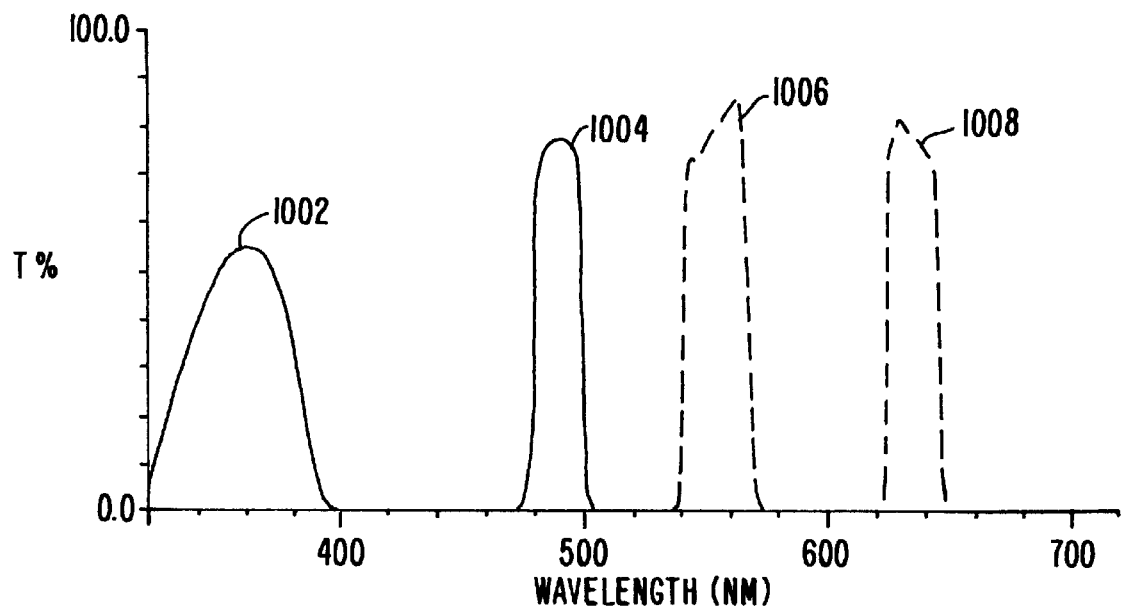
FIG. 10 is a graph illustrating four different excitation filters.

FIG. 10 is a graph illustrating four different excitation filters which could be used as excitation filter 204 in FIG. 2. Preferably, these four filters would be applied to a single substrate, thereby allowing for the simultaneously excitation of at least four different dyes. Comparing FIGS. 8–10 shows that the band of wavelengths transmitted by filter 1002 could be used to excite DAPI without significantly interfering with the emission spectra of DAPI. Similarly, filter 1004 can be used with FITC. Note that while filter 1006 can be used to excite both Cy3 and Cy3++, it coincides with the emission spectra of Cy3. Therefore filter 1006 would be of use only with Cy3++. Although filter 1008 could be used with either Cy5 or Cy5++, it is best suited for use with Cy5++.

Figure 11:
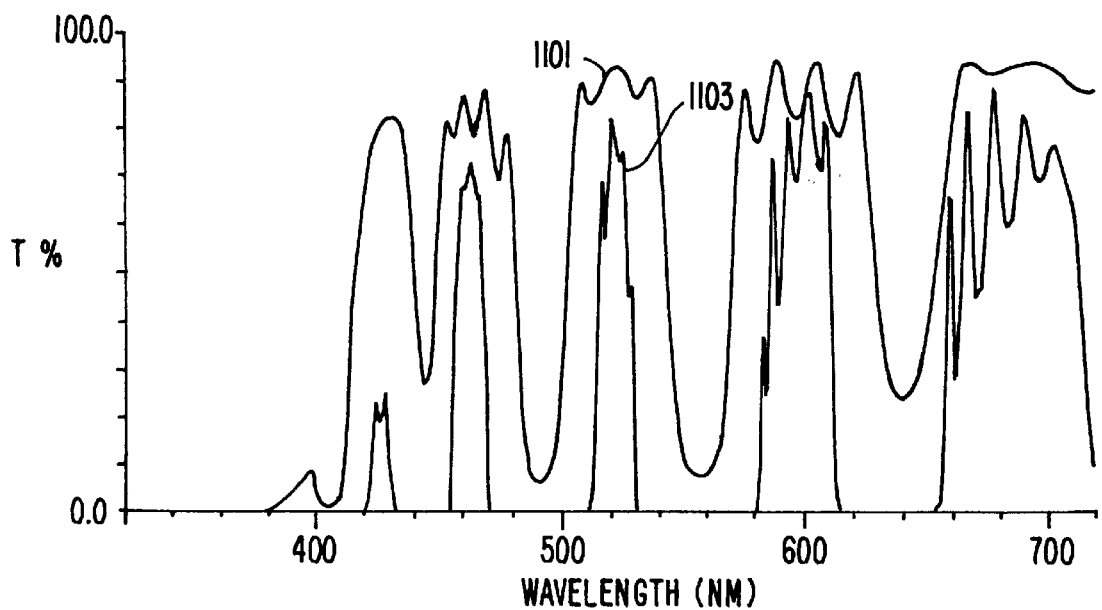
FIG. 11 is a graph of the transmission curves of two filters appropriate for use as a beamsplitter filter and an emission filter.

FIG. 11 is a graph of the transmission curves of two filters appropriate for use as the beamsplitter filter 205 and the emission filter 215 shown in FIG. 2. Curve 1101 is a beamsplitter filter. Comparing this curve to the excitation filters shown in FIG. 10 illustrates that this filter would reflect the wavelength bands passed by curves 1002, 1004, 1006, and 1008 while transmitting the fluorescence emission bands shown in FIG. 9. Emission filter curve 1103 has very narrow pass bands. Comparing this curve with those of FIG. 9 shows that DAPI, FITC, Cy3++, and Cy5++ would all be transmitted by this filter.

Figure 12:
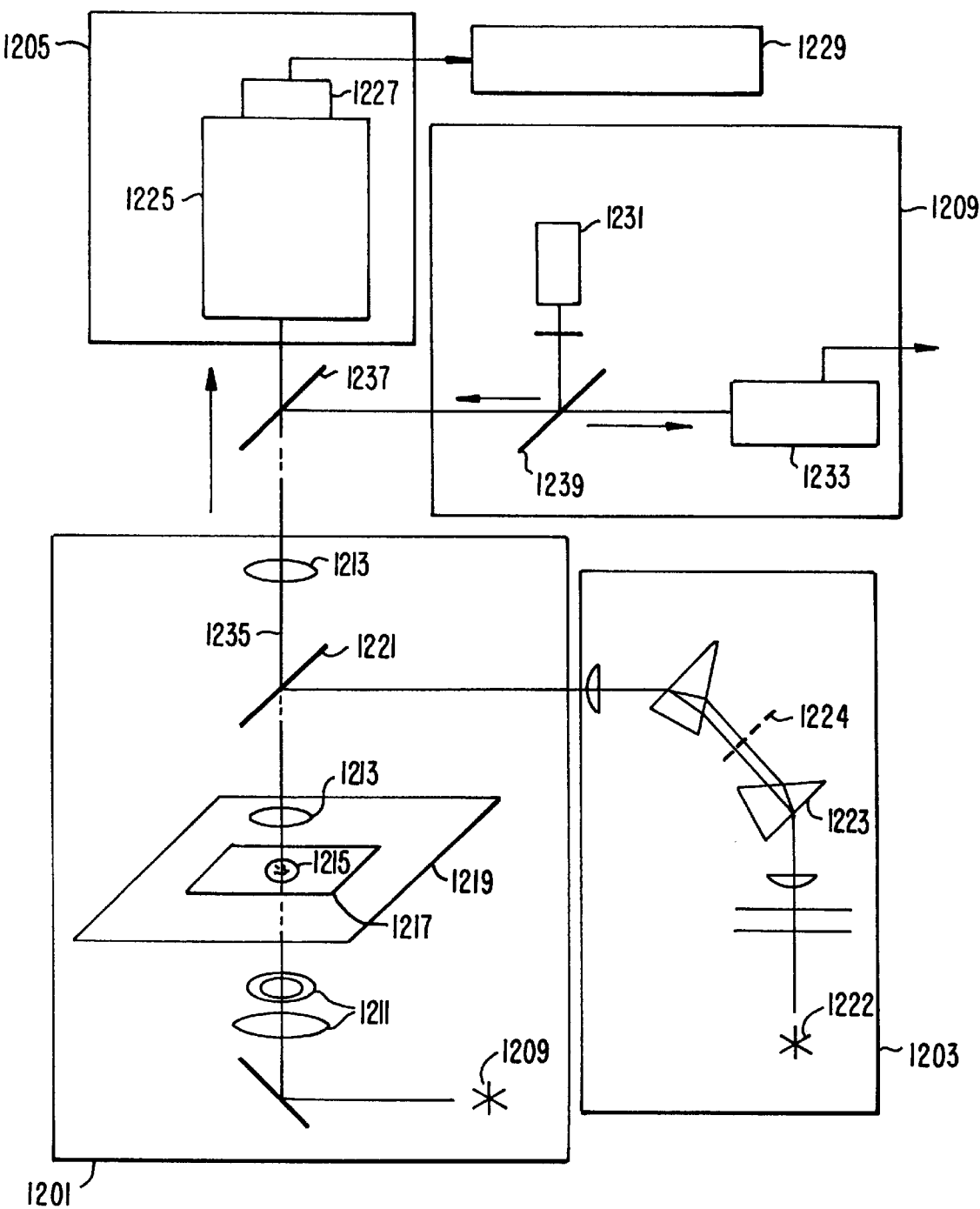
FIG. 12 is an illustration of another embodiment of the invention comprised of an epifluorescence/phase microscope, an excitation source subsystem, a spectral dissection system, and an autofocus, fast metaphase finding system.

FIG. 12 is an illustration of another embodiment of the invention. The system is comprised of an epifluorescence/phase microscope 1201, an excitation source subsystem 1203, a spectral dissection system 1205, and an autofocus, fast metaphase finding system 1207. Subsystem 1201 contains a visible light source 1209, light focusing optics 1211, and imaging optics 1213. Sample 1215 is contained on a slide 1217 which is mounted to a motorized x-y-z stage 1219. Beamsplitter 1221 is used to introduce excitation light from subsystem 1203 onto sample 1215. In this embodiment light from a source 1222 is dispersed using a dispersion element 1223, for example a prism. After the light has been dispersed, it is filtered using a slit plate 1224. The coincidence of the slits on slit plate 1224 with the wavelengths of interest determine the wavelengths which pass through the system, eventually irradiating sample 1215. The width of the slits on plate 1224 determines the bandwidth. Beamsplitter 1221 can also be used to filter the excitation source light by reflecting only those bands of interest. Fluorescence from the excited probes passes into spectral dissection system 1205 which is comprised of an interferometer 1225 and a cooled CCD camera 1227. If necessary, prior to entering interferometer 1225 the fluorescence spectra can be passed through an additional filter (not shown) for further spectral filtering. Data from CCD camera 1227 is sent to computer 1229 for processing. If desired, subsystem 1209 can be used to find areas of interest as well as automatically focus the image. Subsystem 1209 uses a semiconductor laser 1231 and a CCD camera 1233 to determine focus. Light from laser 1231 is sent along the optical path 1235 using a flip mirror 1237. Reflected laser light is passed through beamsplitter 1239 into CCD camera 1233. The output from camera 1233 is used by computer 1229 in conjunction with stage 1219 to focus the image of the slide. This same system can also be used to find areas of potential interest.

As will be understood by those familiar with the art, the present invention may be embodied in other specific forms without departing from the spirit or essential characteristics thereof. Accordingly, disclosure of the preferred embodiment of the invention is intended to be illustrative, but not limiting, of the scope of the invention which is set forth in the following claims.

We claim:

1. An apparatus for imaging labeled chromosome regions, comprising:

a sample containing at least one of said labeled chromosome regions;

an illumination source outputting radiation;

a filter interposed between said sample and said illumination source, said filter eliminating a portion of said outputted radiation, said portion of eliminated radiation unnecessary for exciting said labeled chromosome regions, wherein said filter passes at least a first band of wavelengths to excite said labeled chromosome regions, said excited labeled chromosome regions fluorescing within a second band of wavelengths;

a wavelength selector for spectrally resolving said wavelengths within said second band of wavelengths in a continuously tunable manner;

a detector for detecting said fluorescence within said second band of wavelengths, said detector generating a plurality of output signals dependent upon the intensity of said detected fluorescence; and a monitor for displaying an image of said labeled chromosome regions, said monitor responsive to said output signals.

2. An apparatus for imaging multiple labeled chromosome regions, comprising:

a sample containing at least two of said labeled chromosome regions, the labels of said labeled chromosome regions distinguishable from one another;

an illumination source outputting radiation;

a filter interposed between said sample and said illumination source, said filter eliminating a portion of said outputted radiation, said portion of eliminated radiation unnecessary for exciting said labeled chromosome regions, wherein said filter passes at least a first group of wavelengths, said first group of wavelengths containing bands of wavelengths suitable for simultaneously exciting each label of said labeled chromosome regions, said excited labels fluorescing in a second group of wavelengths containing a band of wavelengths associated with each distinguishable label;

a wavelength selector for spectrally resolving said wavelengths within said second group of wavelengths in a continuously tunable manner;

a detector for detecting said fluorescence within said second group of wavelengths, said detector generating a plurality of output signals dependent upon the intensity of said detected fluorescence; and a monitor for displaying an image of said labeled chromosome regions, said monitor responsive to said output signals.

3. The apparatus of claim 2, further comprising a second filter interposed between said illumination source and said sample, said second filter eliminating IR radiation from said outputted radiation.

4. The apparatus of claim 3, wherein said filter reflects IR radiation.

5. The apparatus of claim 2, further comprising a second filter interposed between said sample and said wavelength selector, said second filter only passing said second group of wavelengths.

6. The apparatus of claim 2, wherein said wavelength selector is an interferometer.

7. The apparatus of claim 6, wherein said interferometer is a common path interferometer.

8. The apparatus of claim 7, wherein said common path interferometer is a monolitic interferometer.

9. The apparatus of claim 6, wherein an interferogram is produced by said interferometer, said interferogram undergoing Fourier transformation to recover the spectral signature of each of said labeled chromosome regions.

10. The apparatus of claim 9, further comprising a data processor for comparing each of said spectral signatures to a library of predetermined spectral signatures in order to identify said label.

11. The apparatus of claim 6, wherein said detector contains a plurality of pixels and said interferometer produces an interferogram for each of said pixels.

12. The apparatus of claim 11, further comprising a data processor for comparing said interferograms to a library of predetermined interferograms in order to identify each of said labels.

13. The apparatus of claim 2, wherein said detector is a CCD detector array.

14. The apparatus of claim 6, further comprising a computer, said computer performing Fourier transformations of the plurality of output signals, said Fourier transformations yielding the wavelength spectra for each pixel of said CCD detector array.

15. The apparatus of claim 2, wherein said image simultaneously contains images of each of said labeled and distinguishable chromosome regions.

16. The apparatus of claim 15, wherein each of said images of said labeled and distinguishable chromosome regions is a different color to each.

17. The apparatus of claim 2, further comprising a focussing system for automatically focussing said sample within said imaging apparatus.

18. The apparatus of claim 2, wherein each chromosome region of said sample is labeled, each of said labels distinguishable from one another.

19. A method of simultaneously imaging multiple labeled chromosome regions, comprising the steps of:

illuminating a sample with a source, said sample containing at least two of said labeled chromosome regions, the labels of said labeled chromosome regions distinguishable from one another, said illumination simultaneously exciting each label of said labeled chromosome regions, said excited labels fluorescing in a group of wavelengths containing a band of wavelengths for each distinguishable label;

spectrally resolving said wavelengths within said group of wavelengths in a continuously tunable manner;

detecting said fluorescence within said resolved wavelengths with a detector, said detector generating a plurality of output signals dependent upon the intensity of said detected fluorescence; and constructing an image of said labeled chromosome regions from said output signals.

20. The method of claim 19, further comprising the step of filtering said source, said filtering step allowing only radiation suitable for exciting said labels to illuminate said sample.

21. The method of claim 19, further comprising the step of filtering the radiation emitted by said sample after said sample is illuminated by said source, said filtering step allowing only radiation within said group of wavelengths to pass.

22. The method of claim 19, wherein said spectral resolving step is performed using an interferometer.

23. The method of claim 22, said method further comprising the steps of:

producing an interferogram of said sample;

Fourier transforming said interferogram;

determining a spectral signature for each label contained in said sample.

24. The method of claim 23, further comprising the step of comparing each spectral signature to a library of predetermined spectral signatures in order to identify each label.

25. The method of claim 22, said method further comprising the steps of:

producing a plurality of interferograms, wherein said detector has a plurality of pixels and each of said interferograms is associated with a pixel;

comparing said interferograms to a library of predetermined interferograms; and identifying each label on the basis of said comparison step.

26. A method of simultaneously imaging multiple labeled chromosome regions, comprising the steps of:

illuminating a sample with a source, said sample containing at least two of said labeled chromosome regions, the labels of said labeled chromosome regions distinguishable from one another, said illumination simultaneously exciting each label of said labeled chromosome regions, said excited labels fluorescing in a group of wavelengths containing a band of wavelengths for each distinguishable label;

spectrally resolving said wavelengths within said group of wavelengths using an interferometer;

detecting said fluorescence within said resolved wavelengths with a detector, said detector generating a plurality of output signals dependent upon the intensity of said detected fluorescence; and constructing an image of said labeled chromosome regions from said output signals.

27. A method of simultaneously imaging multiple labeled chromosome regions, comprising the steps of:

illuminating a sample with a source, said sample containing at least two of said labeled chromosome regions, the labels of said labeled chromosome regions distinguishable from one another, said illumination simultaneously exciting each label of said labeled chromosome regions, said excited labels fluorescing in a group of wavelengths containing a band of wavelengths for each distinguishable label;

spectrally resolving said wavelengths within said group of wavelengths;

detecting said fluorescence within said resolved wavelengths with a detector, said detector generating a plurality of output signals dependent upon the intensity of said detected fluorescence;

constructing an image of said labeled chromosome regions from said output signals;

producing an interferogram of said sample;

Fourier transforming said interferogram; and determining a spectral signature for each label contained in said sample.

28. The method of claim 27, further comprising the step of comparing each spectral signature to a library of predetermined spectral signatures in order to identify each label.

29. A method of simultaneously imaging multiple labeled chromosome regions, comprising the steps of:

illuminating a sample with a source, said sample containing at least two of said labeled chromosome regions, the labels of said labeled chromosome regions distinguishable from one another, said illumination simultaneously exciting each label of said labeled chromosome regions, said excited labels fluorescing in a group of wavelengths containing a band of wavelengths for each distinguishable label;

spectrally resolving said wavelengths within said group of wavelengths;

detecting said fluorescence within said resolved wavelengths with a detector, said detector generating a plurality of output signals dependent upon the intensity of said detected fluorescence;

constructing an image of said labeled chromosome regions from said output signals;

producing a plurality of interferograms, wherein said detector has a plurality of pixels and each of said interferograms is associated with a pixel;

comparing said interferograms to a library of predetermined interferograms; and identifying each label on the basis of said comparison step.

* * * * *